US009091673B2

(12) United States Patent
Fern et al.

(10) Patent No.: US 9,091,673 B2
(45) Date of Patent: Jul. 28, 2015

(54) CARCASS CUTTING METHODS AND APPARATUS

(75) Inventors: Steven Fern, Dunedin (NZ); Alan Dickie, Dunedin (NZ); Scott Clark, Mosgiel (NZ)

(73) Assignee: Robotic Technologies Limited, Dunedin (NZ)

( * ) Notice: Subject to any disclaimer, the term of this patent is extended or adjusted under 35 U.S.C. 154(b) by 897 days.

(21) Appl. No.: 13/262,828

(22) PCT Filed: Apr. 1, 2010

(86) PCT No.: PCT/NZ2010/000062
§ 371 (c)(1),
(2), (4) Date: Oct. 3, 2011

(87) PCT Pub. No.: WO2010/114397
PCT Pub. Date: Oct. 7, 2010

(65) Prior Publication Data
US 2012/0040597 A1    Feb. 16, 2012

(30) Foreign Application Priority Data
Apr. 3, 2009  (NZ) .......................... 576070

(51) Int. Cl.
A22C 17/02    (2006.01)
G01N 33/12    (2006.01)
A22B 5/00     (2006.01)
G01N 23/04    (2006.01)

(52) U.S. Cl.
CPC ............ *G01N 33/12* (2013.01); *A22B 5/0041* (2013.01); *A22C 17/02* (2013.01); *G01N 23/04* (2013.01)

(58) Field of Classification Search
USPC .............. 452/149, 150, 151, 155, 156, 157
See application file for complete search history.

(56) References Cited

U.S. PATENT DOCUMENTS

| 4,209,878 | A | * | 7/1980 | Albert ........................... 452/134 |
| 4,389,749 | A |   | 6/1983 | Korhonen |
| 4,847,954 | A | * | 7/1989 | Lapeyre et al. ............... 452/158 |
| 4,875,254 | A | * | 10/1989 | Rudy et al. .................... 452/157 |
| 5,194,036 | A | * | 3/1993 | Chevalier et al. ............. 452/198 |

(Continued)

FOREIGN PATENT DOCUMENTS

DE   10150394   4/2003
FR   2759866    8/1998

(Continued)

*Primary Examiner* — David Parsley
(74) *Attorney, Agent, or Firm* — Blakely Sokoloff Taylor & Zafman LLP

(57) ABSTRACT

Methods of automated meat processing including an end to end processing method in which carcasses are cut into major portions at a first robotic processing station and into minor portions at robotic processing sub-stations. In one processing method carcass portions are acquired by a robotic arm, imaged and then cuts performed without transfer. In another a first series of processing steps are performed by rotating carcass portions through a plurality of processing stations and a second series of processing steps are performed as carcass portions are advanced along a linear conveyor. In another processing method a plurality of clamps are employed to stabilize a saddle section during a flap cut. In another processing method split pins are used to position a saddle section for a vertebrae cut. In another method a spinal cord is removed by applying a pressurized fluid stream against one end of the spinal cord and applying suction at the other end of the spinal cord.

21 Claims, 12 Drawing Sheets

(56) References Cited

U.S. PATENT DOCUMENTS

| | | | |
|---|---|---|---|
| 5,314,375 A * | 5/1994 | O'Brien et al. | 452/157 |
| 5,372,540 A * | 12/1994 | Burch et al. | 452/156 |
| 5,746,648 A * | 5/1998 | Boeyen et al. | 452/156 |
| 5,853,320 A | 12/1998 | Wathes et al. | |
| RE36,664 E | 4/2000 | O'Brien et al. | |
| 6,354,933 B1 * | 3/2002 | Archambault et al. | 452/135 |
| 7,251,537 B1 * | 7/2007 | Blaine et al. | 700/29 |
| 7,285,040 B2 * | 10/2007 | Ilch et al. | 452/150 |
| 7,404,759 B2 * | 7/2008 | Sato | 452/157 |
| 7,623,249 B2 * | 11/2009 | Sandberg et al. | 356/601 |
| 7,651,388 B2 * | 1/2010 | Faires et al. | 452/157 |
| 7,841,264 B2 * | 11/2010 | Kim et al. | 83/13 |
| 2002/0155803 A1 | 10/2002 | Tieleman | |

FOREIGN PATENT DOCUMENTS

| | | |
|---|---|---|
| GB | 2427121 | 12/2006 |
| WO | WO-2008010732 | 1/2008 |

* cited by examiner

CARCASS CUTTING METHODS AND APPARATUS

CROSS-REFERENCE TO RELATED APPLICATION

The present patent application is a national phase application of International Application No. PCT/NZ2010/000062, filed Apr. 1, 2010.

FIELD OF THE INVENTION

This invention relates to automated methods of cutting an animal carcass and apparatus therefor.

BACKGROUND OF THE INVENTION

There is a general need to automate the processing of animal carcasses into required cuts. The manual butchering of animal carcasses requires skill and judgement in the manipulation of both meat and tools. With skilled staff manual butchering methods are able to produce a relatively high standard of butchered meat product. However, these methods can be time consuming and a considerable amount of training is required to achieve good results. Furthermore, the skill and judgement of the butcher can falter, resulting in an inaccurately butchered meat product and reduced yield or injury to the butcher. Human contact with the carcass also increases the risk of bacterial contamination of the meat product. Manual processing is also costly and working hours may be inflexible.

There has therefore been an effort to automate the butchering of animal carcasses, particularly in large-scale commercial slaughtering/butchering operations. Automated carcass cutting methods have reduced butchering time and butcher injury. However, such systems have been expensive and are typically only capable of performing a limited number of the required processing operations, require transfer between manual and automated processes and are often not adapted to take into account variations between different animal carcasses. Such systems may also create processing bottlenecks—particularly where manual processing cannot be performed at the rate of automated processing.

A significant problem preventing, the full automation of animal carcass cutting operations has been the absence of an end to end system capable of performing all major processing cuts. Prior systems have not been truly integrated so that product and information flows with processing. Whilst X-ray and vision systems have been employed these have not been integrated in an end to end system.

It is an object of the present invention to provide meat processing methods and apparatus overcoming at least some of these disadvantages or to at least provide the public with a useful choice.

SUMMARY OF THE INVENTION

According to one aspect there is provided a method of processing a portion of a carcass including the steps of:
  a. holding a portion of a carcass;
  b. imaging the carcass portion whilst held;
  c. determining one or more cut paths based on the imaging; and
  d. moving the carcass with respect to a cutting tool to cut the carcass along the one or more cut paths.

According to another aspect there is provided a carcass cutting apparatus including:
  a. a grippers for gripping a portion of a carcass;
  b. an imaging system for imaging the portion of a carcass whilst it is held by the grippers;
  c. a control system for determining one or more cut paths based on images from the imaging system; and
  d. a cutting tool for cutting a carcass portion when the grippers move the carcass portion with respect to the cutting tool to cut the carcass along the one or more cut paths.

According to another aspect there is provided a carcass cutting apparatus including:
  a. a robotic arm having grippers for gripping a portion of a carcass;
  b. an imaging system for imaging the portion of a carcass whilst it is held by the robotic arm;
  c. a control system for determining one or more cut paths based on images from the imaging system; and
  d. a cutting tool for cutting a carcass portion when the robotic arm moves the carcass portion with respect to the cutting tool to cut the carcass along the one or more cut paths.

According to another aspect there is provided a method of removing a spinal cord from a carcass portion in which the spinal cord has been cut at each end including the steps of:
  a. applying a pressurised fluid stream against one end of the spinal cord; and
  b. applying suction at the other end of the spinal cord.

According to another aspect there is provided a method of performing a longitudinal cut along a saddle section of a carcass including the steps of:
  a. locating the spine of the saddle section between supports;
  b. locating pins in either end of the spinal column; and
  c. guiding the saddle section through a cutting tool to cut longitudinally through the spinal column to cut the saddle section in half.

According to another aspect there is provided a method of cutting a saddle section of a carcass including the steps of:
  a. supporting the saddle section upon a support;
  b. clamping the ribs of the saddle section by a plurality of clamps to clamp the ribs between the clamps and the support; and
  c. cutting the carcass whilst so clamped.

According to another aspect there is provided a method of processing a carcass including the steps of:
  a. cutting a carcass into major portions at a first robotic processing station; and
  b. conveying the major portions to a plurality of robotic processing sub-stations where the major portions are processed into minor portions.

According to another aspect there is provided a method of processing carcass portions comprising:
  a. loading carcass portions onto a rotary carousel;
  b. rotating the carcass portions through a plurality of stations at which each carcass portion is processed; and
  c. transferring the carcass portions to a linear conveyor for further processing.

According to another aspect there is provided a meat processing system including:
  a. a rotary carousel having a plurality carcass support arms rotatable through a plurality of processing stations at which carcass processing is performed; and
  b. a linear conveyor which transfers carcass portions for further processing at one or more further processing station.

According to another aspect there is provided a method of performing a plurality of sequential cuts on a carcass using computer controlled cutting apparatus including the steps of:

a. imaging the carcass to obtain imaging information;
b. determining cutting co-ordinates for the carcass based on the imaging information; and
c. maintaining geometric reference between the carcass and cutting apparatus to perform the sequence of cuts based on the imaging information.

BRIEF DESCRIPTION OF THE DRAWINGS

The accompanying drawings which are incorporated in and constitute part of the specification, illustrate embodiments of the invention and, together with the general description of the invention given above, and the detailed description of embodiments given below, serve to explain the principles of the invention.

DETAILED DESCRIPTION OF EMBODIMENTS OF THE INVENTION

Figure 1:
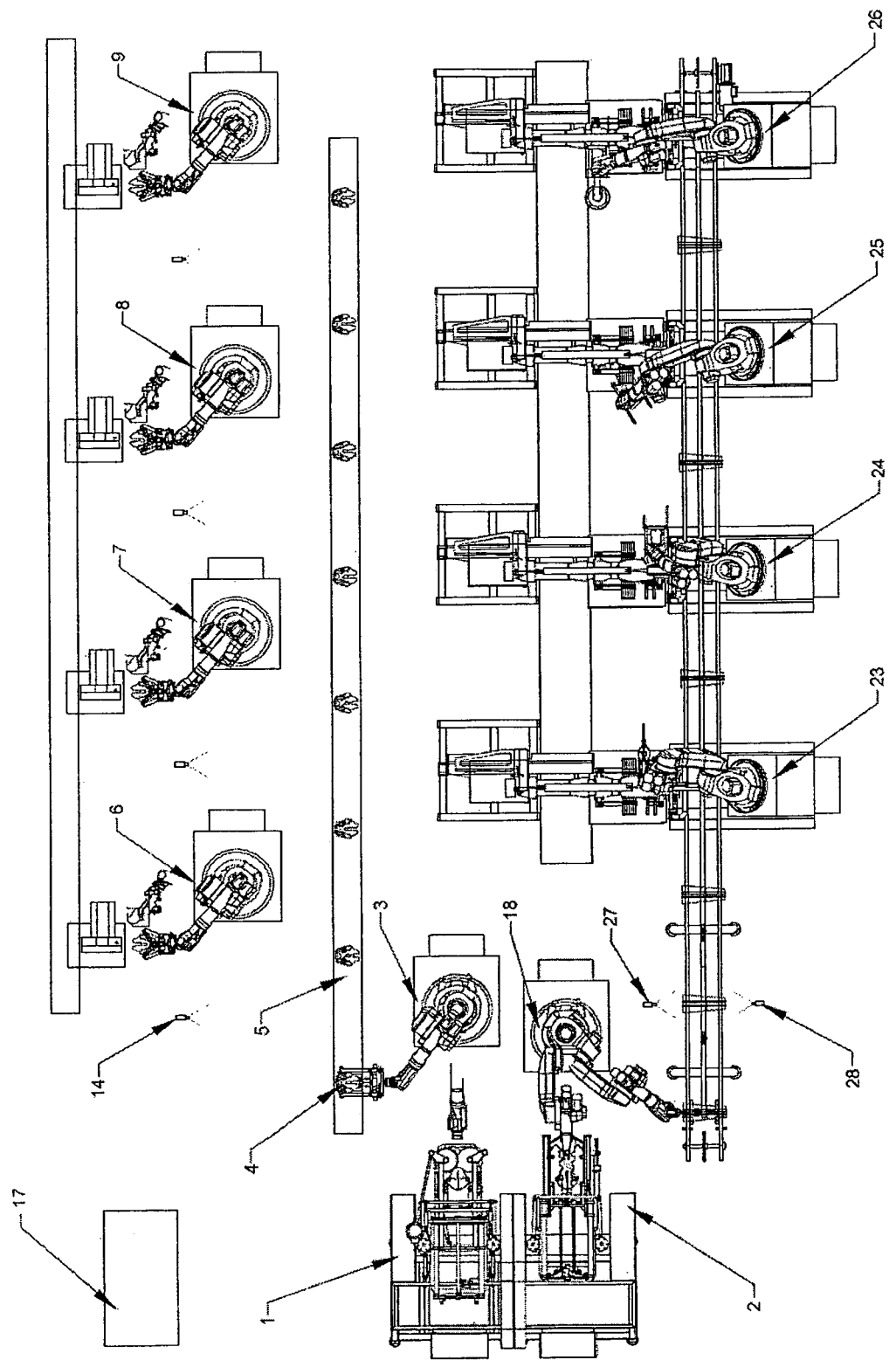
FIG. 1 shows a plan view of a meat processing system including primal cutting stations and fore-quarter and saddle cutting stations.

FIG. 1 shows an integrated system for performing primal cuts and then processing the saddle portions and fore-quarters at a number of stations matched to the processing room capacity. Prior to processing by the system shown in FIG. 1 a carcass may be X-rayed to reveal the internal anatomy of the carcass using a system such as that described in WO 2008010732, the disclosure of which is hereby incorporated by reference. The anatomical information obtained by X-ray imaging may be associated with a carcass and used in subsequent processing as will be described.

The system shown in FIG. 1 includes a fore-quarter primal cutting station 1 which may utilize a carcass cutter as described in the applicant's prior application GB2445277A, the disclosure of which is hereby incorporated by reference. A saddle cutting station 2 may utilize a carcass cutter as described in the applicant's prior application WO2006/135262, the disclosure of which is hereby incorporated by reference.

A robotic arm 3 transfers a fore-quarter section 4 from fore-quarter primal cutting section 1 to conveyor 5. Whilst robotic arms 3 and 18 are shown in this embodiment simpler purpose-built transfer mechanisms could be employed. Robotic arm 3 may place fore-quarter section cut side down so that it sits in a known orientation on conveyor 5. Conveyor 5 may be indexed so that robotic arms 6 to 9 may acquire a fore-quarter section at a known position on the conveyor. Alternatively sensors may be used to detect the position of a fore-quarter section and acquire it. Alternatively fore-quarter sections could be deposited into containers on a conveyor adapted to hold the fore-quarter sections in a desired orientation.

Figure 2:
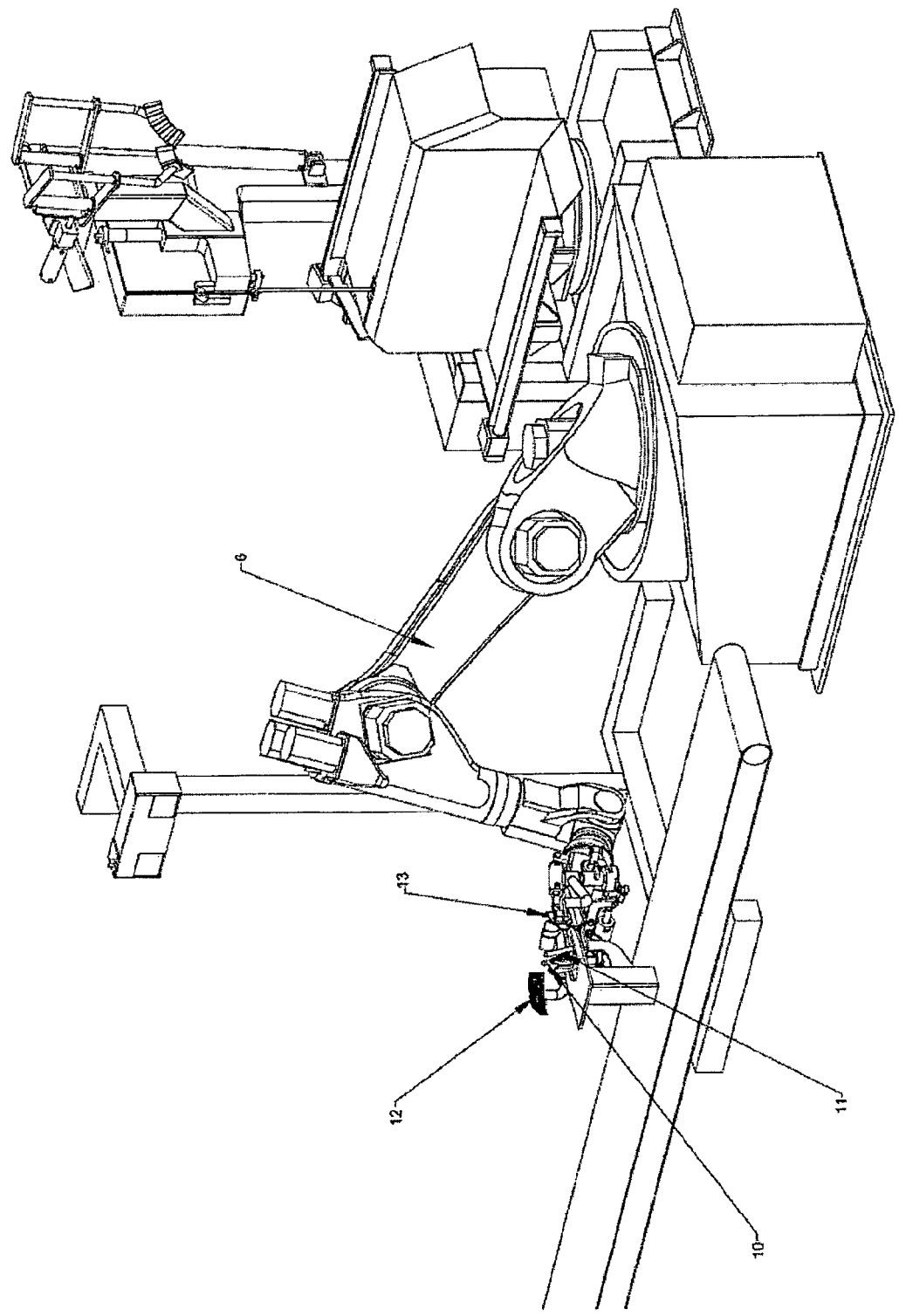
FIG. 2 shows a perspective view of a fore-quarter cutting station with the robotic arm acquiring a fore-quarter section.

Referring now to FIG. 2 a fore-quarter cutting station is shown in more detail. Robotic arm 6 has spaced apart rests 10 and 11 adapted to be positioned inside the fore-quarter section with the spinal column position between them. Clamps 12 and 13 may be driven towards rests 10 and 11 to clamp the fore-quarter section between them. In use robotic arm 6 is positioned as shown in FIG. 2 so that it may come from below to position rests 10 and 11 internally against the spinal column and clamps 12 and 13 may then be driven towards rests 10 and 11 to clamp the fore-quarter section to robotic arm 6.

Figure 3:
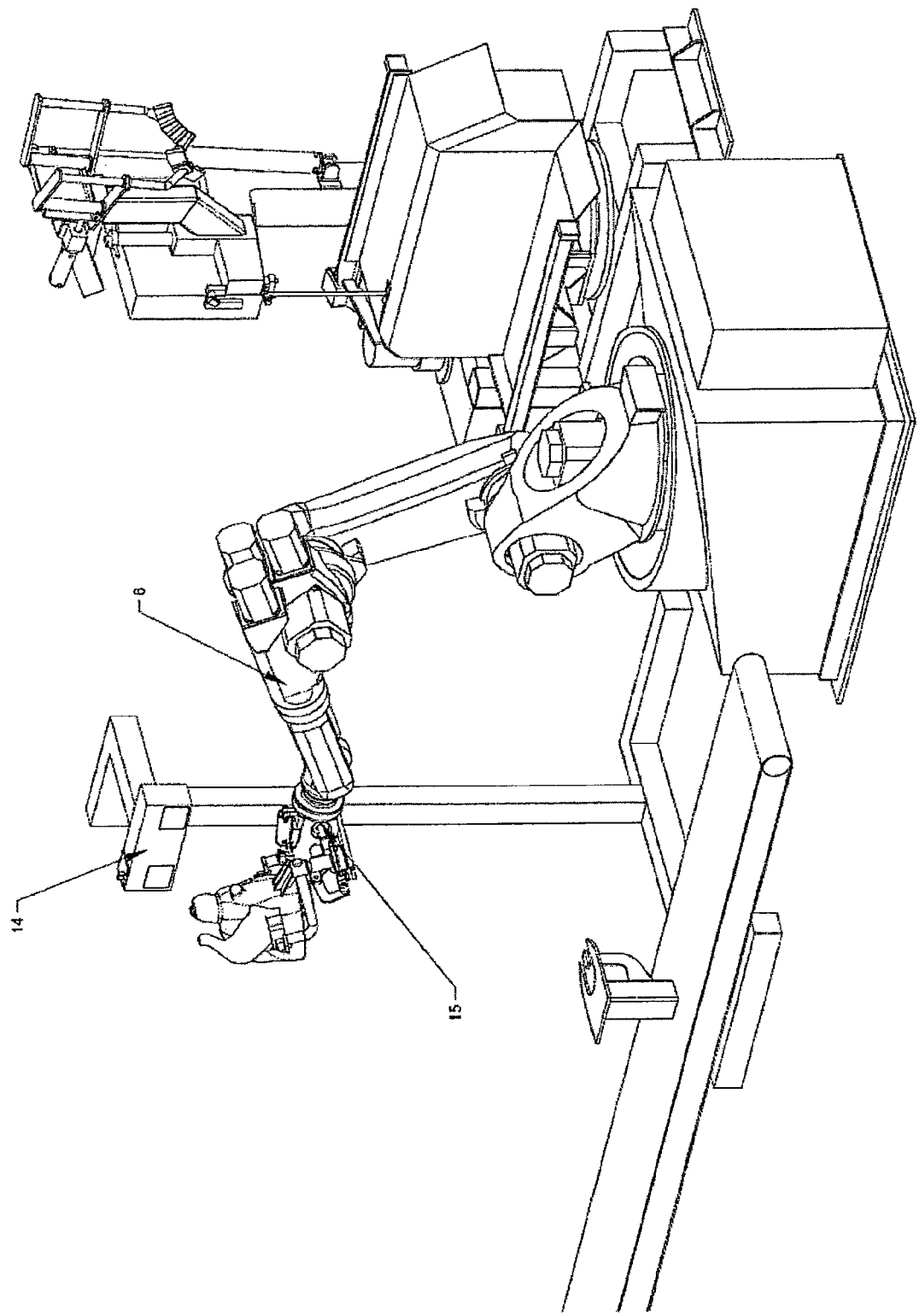
FIG. 3 shows a perspective view of a fore-quarter cutting station with the fore-quarter section being imaged.
Figure 4:
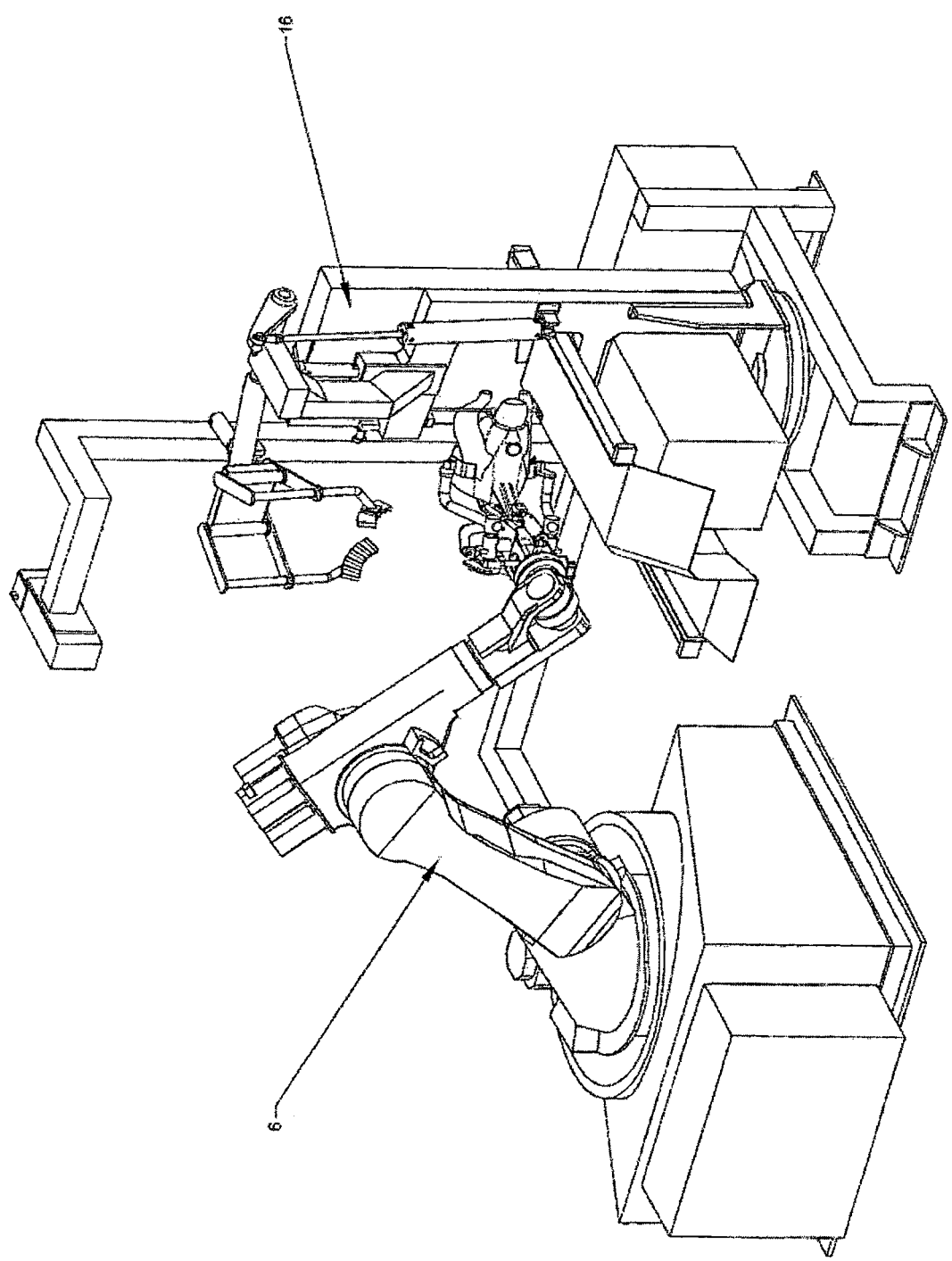
FIG. 4 shows a perspective view of a fore-quarter cutting station with the fore-quarter section being cut.

Once the fore-quarter section is firmly secured to robotic arm 6 the fore-quarter section is moved to be imaged by optical imaging apparatus 14 as shown in FIG. 3. The type of images and the number acquired will depend upon the type of cut to be performed. For a shank cut a single image could be sufficient whereas for other cuts it is preferable that a number of images are obtained and a three dimensional or at least a pseudo three dimensional model is developed. One preferred approach is to rotate the fore-quarter section through four 90 degree rotations so as to obtain two dimensional images from four sides. These images and the previously acquired X-ray images may be stored in control system 17 which may be a centralised or distributed control system. From these images a three dimensional or at least a pseudo three dimensional model may be developed and cutting paths calculated by control system 17 based on the model. X-ray imaging information previously acquired may be used alone or in combination with optical imaging to determine cutting paths for certain cuts.

The imaging apparatus may project structured light onto the fore-quarter section and multiple images may be acquired to develop a true three dimensional model. To achieve this a laser line may scan across the fore-quarter section with images captured at regular intervals to acquire a true three dimensional image in each orientation.

A datum referencing device 15 in the form of three orthogonally disposed reference points (balls in this case) may be attached to the end of robotic arm 6 so that the images captured by imaging apparatus 14 may be referenced to the robotic arm.

After imaging the robotic arm 6 moves the fore-quarter section with respect to the blade of a bandsaw 16 to perform any or all of a knuckle cut, neck cut, brisket cut, shank cut, vertebrae split, and any other desired cut. Depending upon the arrangement the bandsaw may be rotatable through 90 degrees to facilitate the vertebrae split.

It is to be appreciated that from the fore-quarter section being acquired by robotic arm 6 it is continuously held in a fixed relationship to robotic arm 6 throughout imaging and multiple cutting operations; thus avoiding the need to re-index the position of the fore-quarter section with respect to the robotic arm which would occur were the fore-quarter section to be transferred between the various operations.

Figure 5:
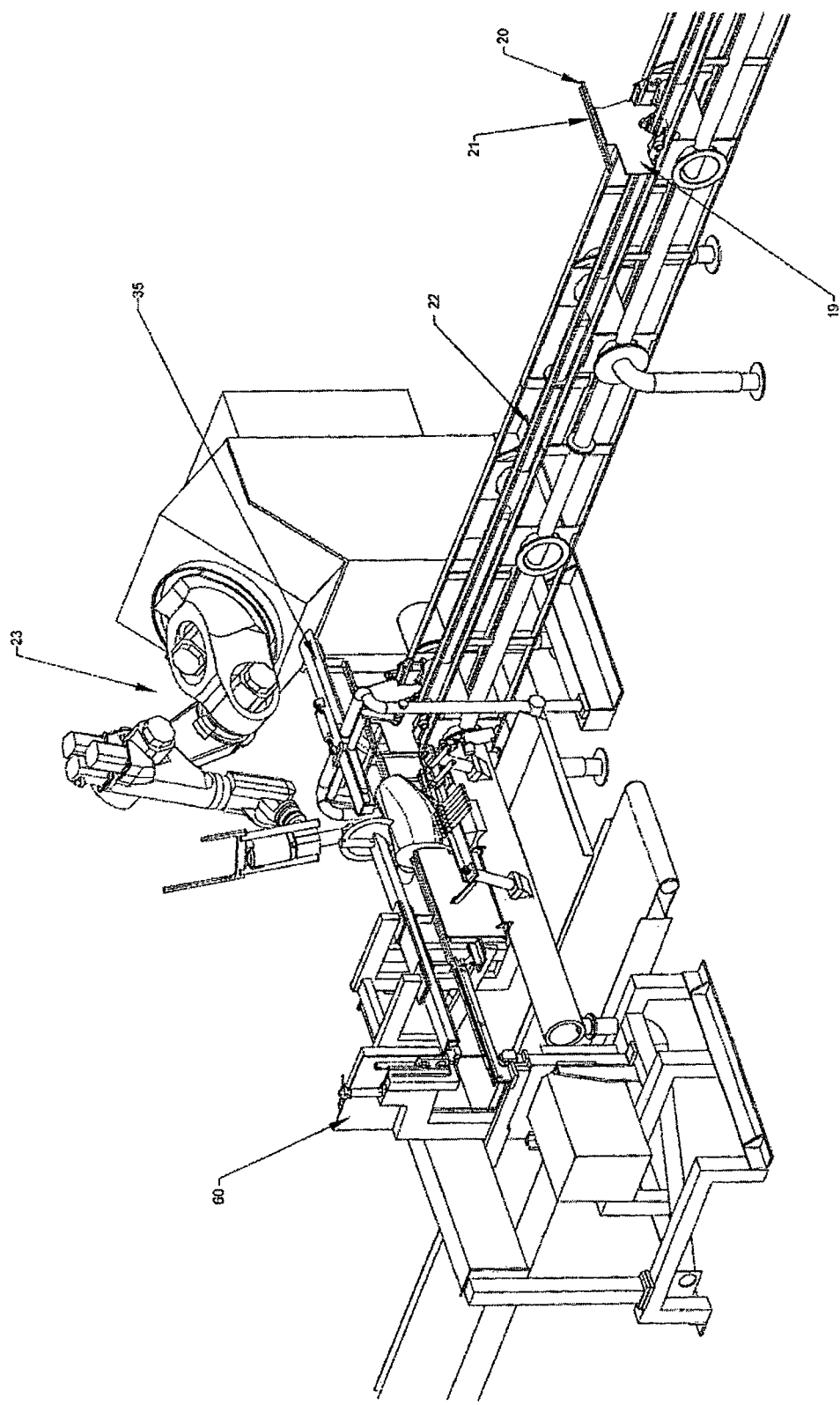
FIG. 5 shows a perspective view of a saddle cutting station.

Referring now to FIGS. 1 and 5 a saddle cutting station is shown. Robotic transfer arm 18 transfers a saddle section from saddle primal station 2 to a support 19. Support 19 has spaced apart rods 20 and 21 to support the spinal column therebetween. A number of such supports 19 are advanced along track 22 to supply respective saddle cutting stations 23 to 26. As the supports are advanced each end of the saddle section is imaged by cameras 27 and 28 and the images supplied to control system 17.

Figure 6:
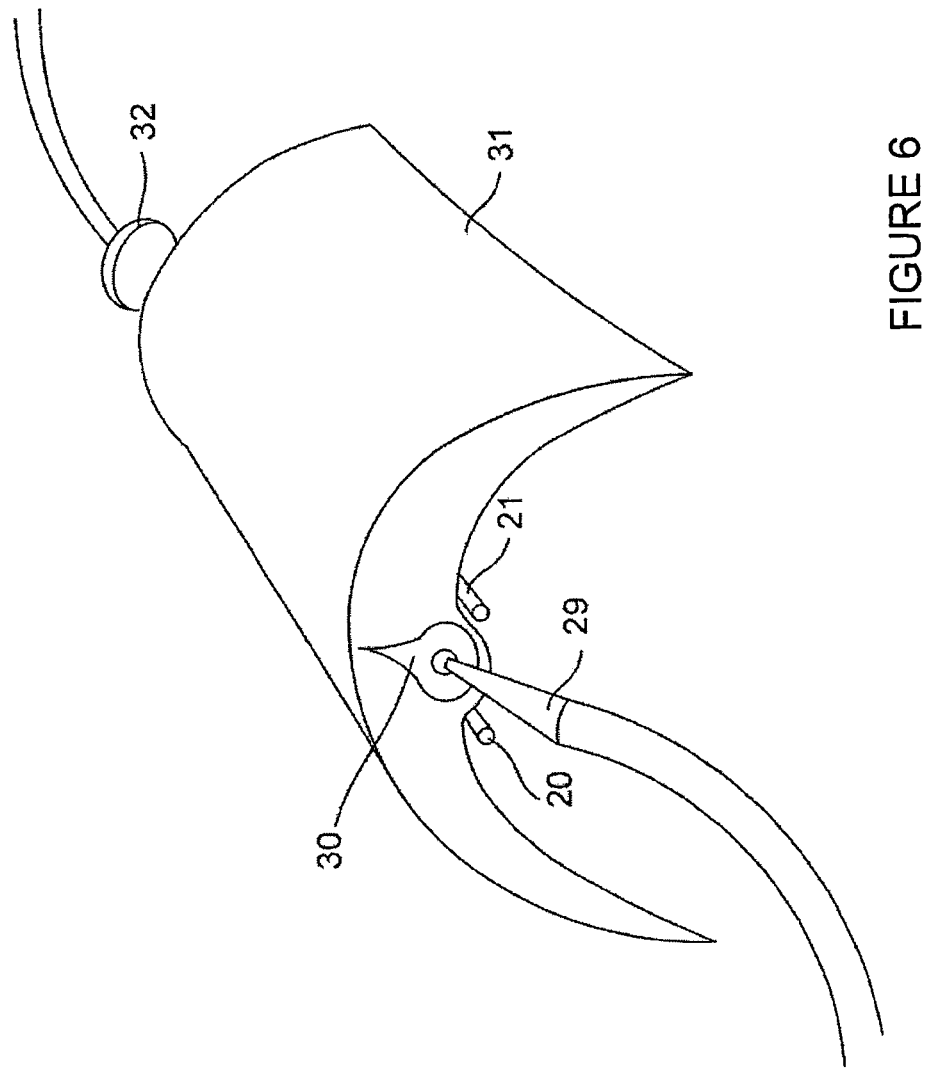
FIG. 6 shows a schematic diagram of a system for removing a spinal cord.

After imaging the spinal cord is removed as shown schematically in FIG. 6. A probe 29 it inserted into spinal column 30 of saddle section 31 and supplies pressurized fluid into the spinal column to urge the spinal cord along the spinal column. A cup 32 is placed over the other end of the spinal column and a vacuum is applied to suck out the spinal cord. The combination of pressurized fluid at one end and suction at the other has been found to be effective to remove the spinal cord without requiring the spinal column to be cut.

The probe 29 and cup 32 may be positioned according to standard anatomical positioning for a particular species where supports 20 and 21 centralise the spinal column to an acceptable tolerance or alternatively they may be positioned utilizing imaging information from cameras 27 and 28 and suitable positioning mechanisms.

Figure 7:
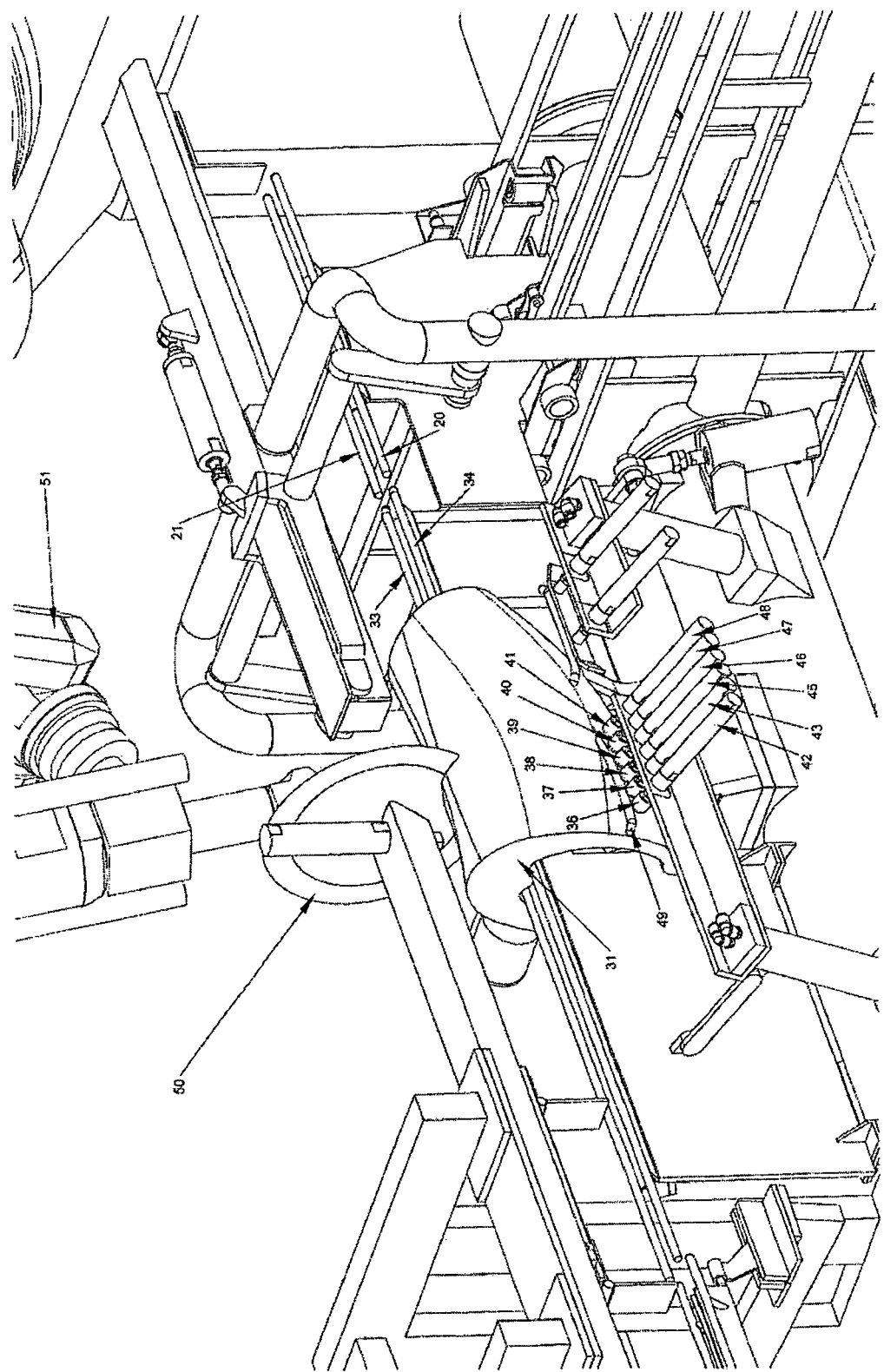
FIG. 7 shows an enlarged view of the saddle cutting station shown in FIG. 5 performing a cross cut.

Once the spinal column is removed support 19 advances to a saddle cutting station, station 23 in this case as shown in FIG. 7. The saddle section 31 is then transferred from rails 20 and 21 to rails 33 and 34 by pusher 35 pushing saddle section 31 from behind to the required position for a cross cut to be performed. The cross cut may be calculated based on X-ray information so as to separate the rack and loin at the best location based on the positions of the bones.

Figure 8:
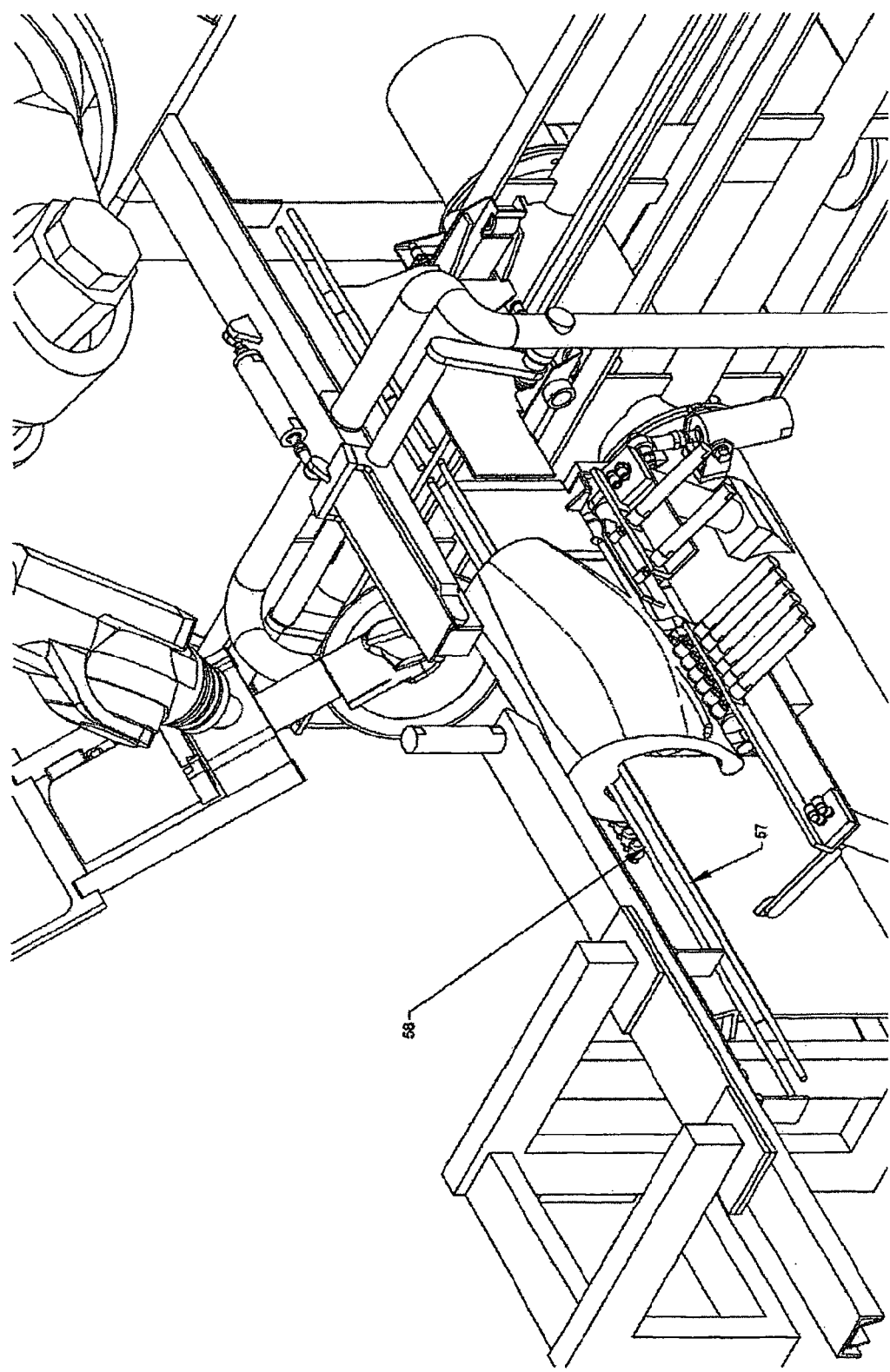
FIG. 8 shows an enlarged view of the saddle cutting station shown in FIG. 5 performing a flap cut.

When the saddle section 31 is in the desired position it may be held via a plurality of grippers 36 to 41 actuated by hydraulic or pneumatic rams 42 to 48 which hold the ribs of saddle section 31 against bar 49 so as to firmly hold the saddle section 31 during cross and flap cuts. A similar gripping arrangement is provided on the opposite side. The use, of multiple grippers has been found to hold the ribs of the flaps more effectively than a single gripper. As shown in FIG. 7 a cross cut is performed by moving a cutting blade 50 attached to robotic arm 51 across the saddle section 31. The saddle section has been placed in the correct position for the cut by pusher 35 based upon X-ray information obtained before processing. A flap cut is then performed, as shown in FIG. 8, by manipulating cutting blade 50 to a desired height via robotic arm 51 according to a cutting path determined by locating the eye fillet from the images obtained by cameras 27 and 28.

Figure 9:
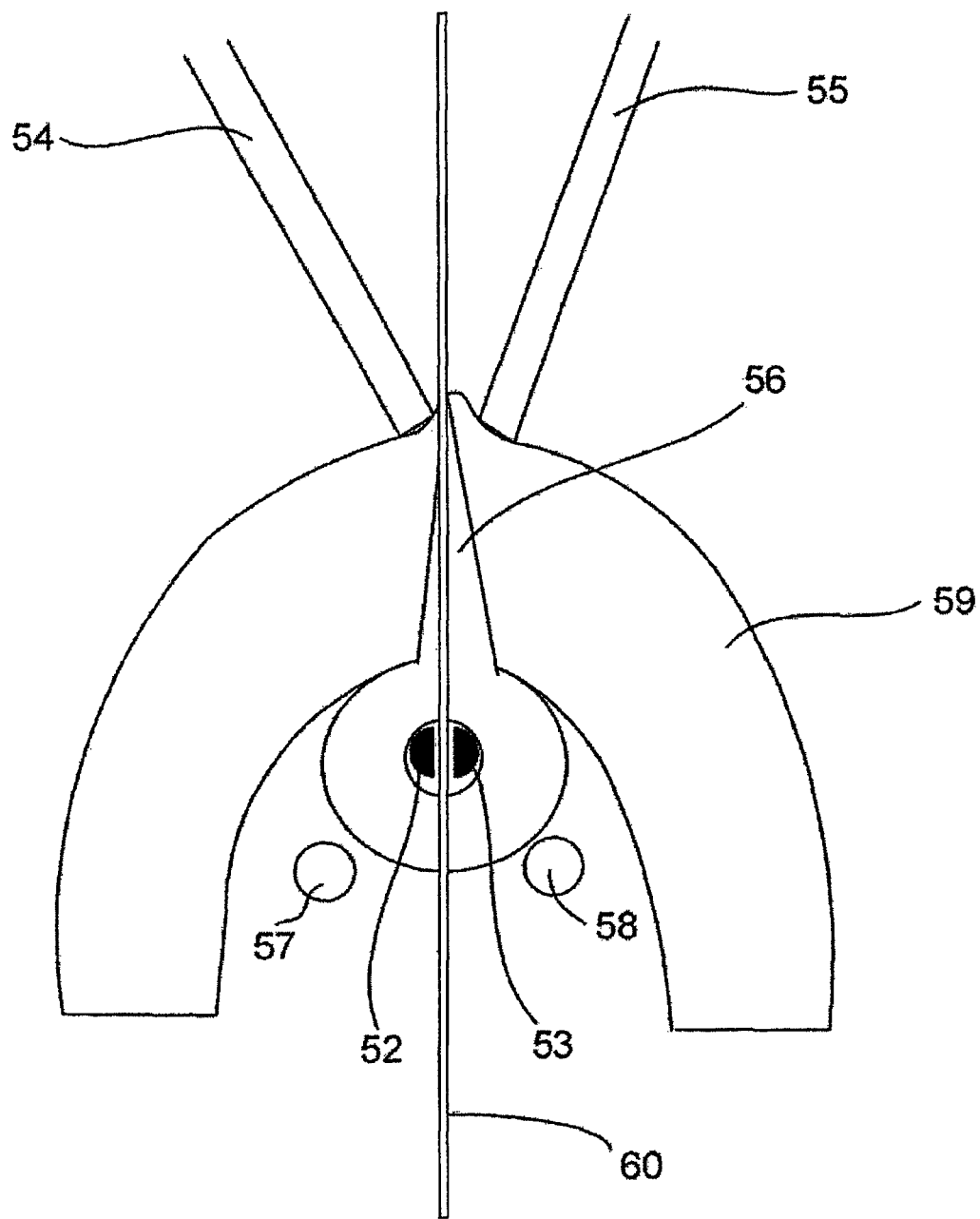
FIG. 9 shows a method for performing a vertebrae cut.

Finally a vertebrae cut is performed as shown in FIGS. 5 and 9 by inserting a split pin having tines 52 and 53 into the spinal column of a saddle subsection 59 (after the cross and flap cuts) and lowering locators 54 and 55 to vertically orient feather bones 56. A similar split is inserted in the other end. The split pins and locators are then advanced to draw saddle subsection 59 through bandsaw 60 with the blade passing between the tines 52 and 53 (and the pair at the other end) and locators 54 and 55. In this way the saddle subsection may be accurately cut along the middle of the spinal column.

Figure 10:
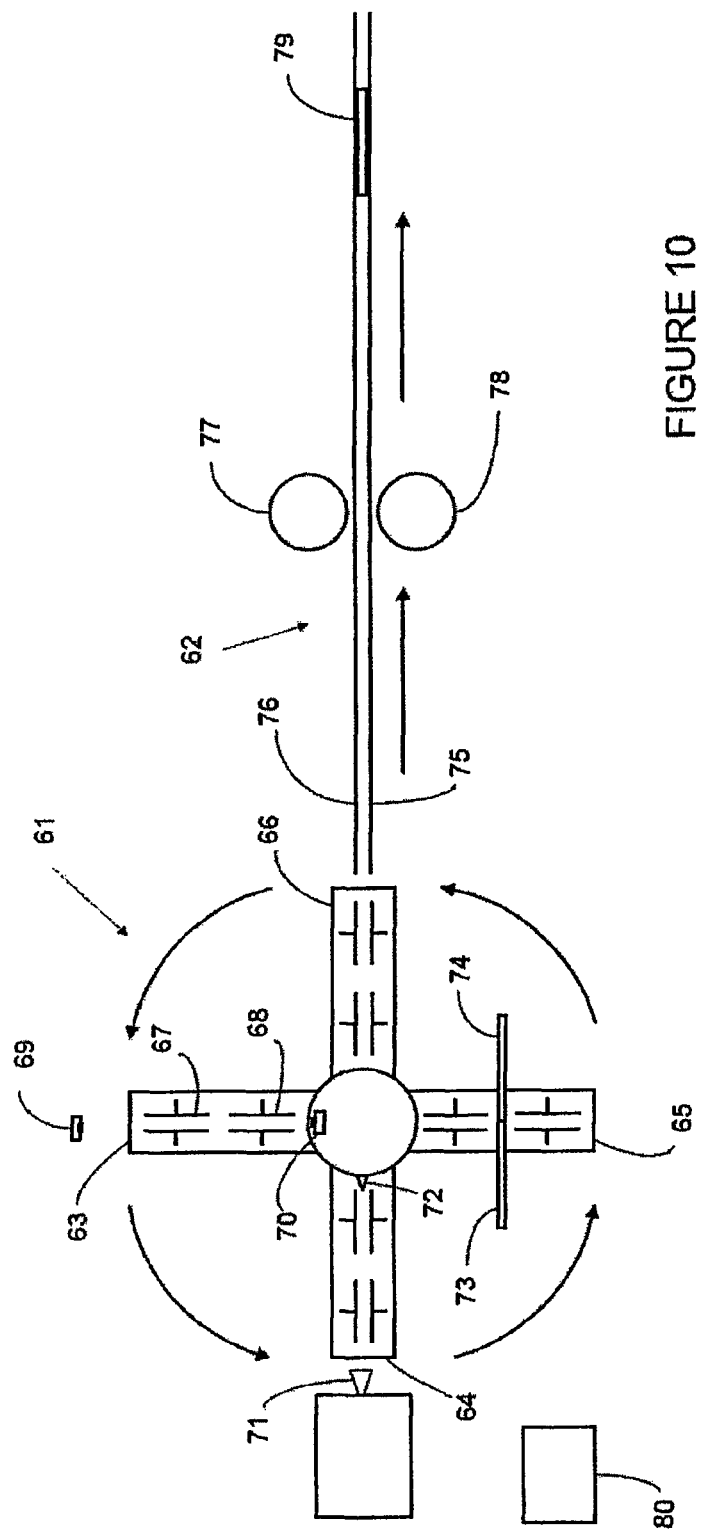
FIG. 10 shows a meat processing system employing a rotary carousel and linear conveyor.
Figure 11:
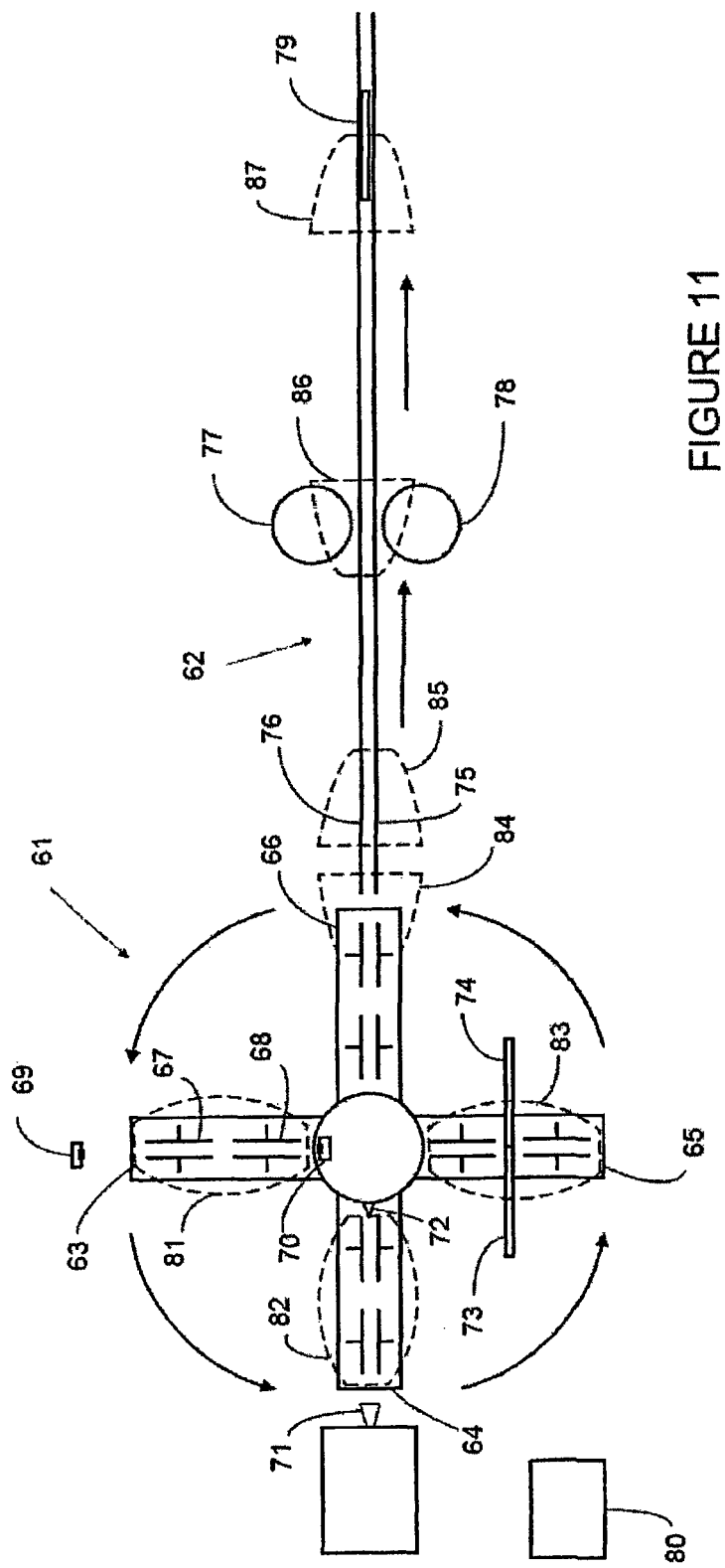
FIG. 11 shows a carcass portion being processed by the meat processing system shown in FIG. 10.

Referring now to FIGS. 10 and 11 a meat processing system employing a rotary carousel 61 and a linear conveyor 62 will be described. FIG. 11 shows carcass portions in dashed outline overlaying the system shown in FIG. 10 to illustrate its operation. Rotary carousel 61 has four support arms 63 to 66, each having a pair of spaced apart pairs of support rails 67 and 68. As shown in FIG. 9 the spine of a carcass portion locates between the support rails to position a carcass portion in a desired orientation and position. The carousel 61 is rotated 90° anticlockwise between processing operations so that each support arm moves to the next processing station.

In FIG. 10 support arm 63 is shown at the first processing station where a carcass 81 is imaged by cameras 69 and 70 at either end of the carcass. Further imaging from different perspectives, including X-ray imaging, may be performed to assist cut path calculation. This information is supplied to controller 80 and is used in subsequent processing. The cut specifications (e.g. flap cut height etc.) may be entered by a user into controller 80 and different cuts and cut specifications may be utilised for different carcasses. Carcass portion 82 has been imaged and spinal cord removal devices 71 and 72 are positioned based on imaging information supplied to controller 80. These devices operate generally in the manner described in relation to FIG. 6. Carcass 83 is cut into the rack saddle and shortloin saddle by circular cutting blades 73 and 74 at the third station. Carcass portions 84 and 85 are transferred from support arm 66 to spaced apart rails 75 and 76 at the forth station and may be transferred therealong by pushers, conveyor belts or the like. Throughout processing on the rotary carousel the carcass maintains a known geometric orientation to the processing apparatus at each processing station. When the carcass is transferred to the rails the pushers locate the end of the carcass to maintain a known geometric reference for further processing.

The carcass portions may be continuously advanced along linear conveyor 62 and processed as they move or may be stopped for processing at certain locations or a combination of both. Carcass portion 86 may be advanced through rotary cutter blades 77 and 78 to perform brisket and or flap cuts or carcass portion 86 may be held in a stationary position and apparatus of the type shown in FIG. 7 may be employed to perform these cuts. Carcass portion 87 may be advanced through circular cutting blade 79 to perform a cut along the spinal cord or carcass 87 may be held stationary and the blade 79 moved relative to carcass 87.

Figure 12:
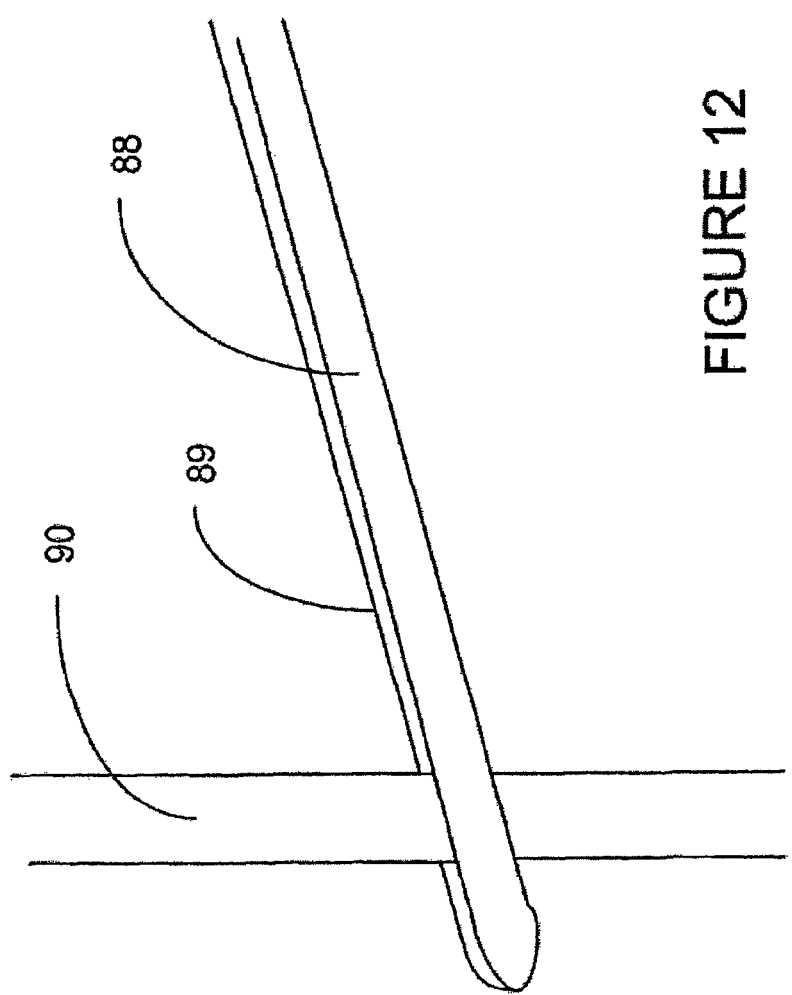
FIG. 12 shows a guide and saw arrangement for performing a vertebrae cut.

FIG. 12 shows an arrangement that may be used to perform a spinal cut. A pair of spaced apart guide rods 88 and 89 have a gap therebetween to accommodate a blade, in this case a bandsaw blade 90. Rods 88 and 89 may be long enough to pass through an entire spinal cavity and serve to guide blade 90 along the spinal column.

There are thus provided an integrated automated meat processing system allowing fully automated end to end processing. By allowing scalability of sub-processing stations to the desired processing rate equipment utilization may be optimized and bottlenecks avoided. As information flows with processing it may be used and combined with additional information at each stage of processing. This arrangement also provides enhanced traceability of product to each sub-processing station.

Fully automated processing provides increased accuracy resulting in enhanced product yield and value. This may be achieved using X-ray and optical information, optimized cutting path calculation and robotic accuracy. Robotic processing avoids labour related expenses and allows greater flexibility in operating schedules.

By minimizing product transfer multiple processing steps may be performed without requiring re-indexing of the carcass portion position and orientation with respect to processing equipment. By imaging a carcass portion whilst it is held by a robotic arm cutting paths may be easily determined with respect to the robotic arm without requiring indexing of image information to a robotic arm where a carcass portion is acquired after imaging.

There is also provided a method of effectively removing the spinal cord without requiring splitting of the spinal column.

While the present invention has been illustrated by the description of the embodiments thereof, and while the embodiments have been described in detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the applicant's general inventive concept.

The invention claimed is:

1. A method of processing a portion of a carcass including the steps of:
   a. holding a portion of a carcass using a robotic arm;
   b. imaging the carcass portion whilst held by the robotic arm;
   c. determining one or more cut paths based on the imaging; and
   d. the robotic arm having plural degrees of freedom and moving the carcass with respect to a cutting tool to cut the carcass along the one or more cut paths, wherein the portion of a carcass is held by the robotic arm throughout processing.

2. A method as claimed in claim 1 wherein the carcass portion is moved to a plurality of positions to obtain multiple images of the carcass from different perspectives.

3. A method as claimed in claim 2 wherein a three dimensional image of the carcass portion is generated from the images obtained.

4. A method as claimed in claim 1 wherein structured light is scanned over the carcass portion as the images are obtained.

5. A method as claimed in claim 1 wherein a datum referencing element is provided on the robotic arm so that during imaging the carcass portion and datum referencing element are captured and the datum referencing element is used to determine the position and orientation of the carcass with respect to the robotic arm.

6. A method as claimed in claim 5 wherein the datum referencing element consists of 3 reference points orthogonally disposed with respect to the robotic arm.

7. A method as claimed in claim 1 wherein an X-ray image of the carcass portion is obtained prior to processing using the robotic arm and the X-ray image is combined with imaging of the carcass portion whilst held by the robotic arm to form a composite model of the carcass portion.

8. A method as claimed in claim 7 wherein cut paths are determined based on the composite model.

9. A method as claimed in claim 1 wherein multiple cuts are performed whilst the carcass portion is continuously held.

10. A method as claimed in claim 9 wherein the carcass portion is a fore-quarter section of a carcass.

11. A method as claimed in claim 10 wherein the cuts are selected from the group consisting of knuckle cut, neck cut, brisket cut, shank cut and vertebrae split.

12. A method as claimed in claim 1 wherein the cutting tool is a bandsaw.

13. A method as claimed in claim 1 wherein the carcass portion is gripped by clamps.

14. A method as claimed in claim 1 wherein the carcass is secured to a movable conveyor and moved on the conveyor between a plurality of positions at which the carcass is cut.

15. A method of performing a plurality of sequential cuts on a carcass using a robotic arm having plural degrees of freedom and a cutting tool including the steps of:
   a. imaging the carcass whilst it is held by the robotic arm to obtain imaging information;
   b. determining cutting co-ordinates for the carcass based on the imaging information; and
   c. maintaining geometric reference between the carcass and cutting tool to perform the sequence of cuts based on the imaging information by the robotic arm retaining hold.

16. A method as claimed in claim 15 wherein the imaging includes optical imaging.

17. A method as claimed in claim 15 wherein the imaging includes X-ray imaging.

18. A method as claimed in claim 15 wherein geometric reference between the carcass and cutting apparatus is maintained by retaining hold of the carcass portion by the robotic arm throughout the performance of imaging and cutting steps.

19. A method as claimed in claim 15 wherein geometric reference between the carcass and cutting apparatus is maintained by maintaining the carcass portion in a known position and orientation with respect to a conveyor throughout processing.

20. A method as claimed in claim 15 wherein cuts are performed according to selected cut specifications.

21. A method as claimed in claim 15 wherein the cuts performed on a carcass portion can be dynamically adjusted.

* * * * *